(12) United States Patent
Muller et al.

(10) Patent No.: US 12,605,792 B2
(45) Date of Patent: Apr. 21, 2026

(54) CORNEAL TREATMENT

(71) Applicant: Allotex, Inc., Boston, MA (US)

(72) Inventors: David Muller, Boston, MA (US); Michael Mrochen, Eglisau (CH)

(73) Assignee: Allotex, Inc., Boston, MA (US)

( * ) Notice: Subject to any disclaimer, the term of this patent is extended or adjusted under 35 U.S.C. 154(b) by 551 days.

(21) Appl. No.: 17/440,961

(22) PCT Filed: Mar. 18, 2020

(86) PCT No.: PCT/US2020/023331
§ 371 (c)(1),
(2) Date: Sep. 20, 2021

(87) PCT Pub. No.: WO2020/191030
PCT Pub. Date: Sep. 24, 2020

(65) Prior Publication Data
US 2022/0161370 A1      May 26, 2022

Related U.S. Application Data

(60) Provisional application No. 62/819,769, filed on Mar. 18, 2019.

(51) Int. Cl.
*A61F 2/14*        (2006.01)
*B23K 26/0622*        (2014.01)
(Continued)

(52) U.S. Cl.
CPC ............ *B23K 26/402* (2013.01); *A61F 2/142* (2013.01); *B23K 26/0624* (2015.10); *G16H 20/40* (2018.01); *A61F 2240/002* (2013.01)

(58) Field of Classification Search
CPC ... B23K 26/402; B23K 26/0624; A61F 2/142; A61F 2240/002; A61F 2009/00882;
(Continued)

(56) References Cited

U.S. PATENT DOCUMENTS 5,779,696 A * 7/1998 Berry ...................... A61F 9/008
606/5
6,063,072 A * 5/2000 Muller .................. A61F 9/0081
606/17
(Continued)

*Primary Examiner* — Scott M. Getzow
(74) *Attorney, Agent, or Firm* — McDonnell Boehnen Hulbert & Berghoff LLP

(57) ABSTRACT

Systems and methods produce implants for treating keratoconus or other eye disorders. An example method includes identifying a subject with keratoconus. The method includes obtaining, with assessment means, an assessment of a cornea of a subject; determining, by processor(s), inverse measurements for correcting one or more irregularities associated with the keratoconus based on the assessment; and shaping, with a laser system, a donor cornea according to a pattern based on the inverse measurements. The example method may further include determining smoothing effects associated with the cornea, wherein the inverse measurements are based further on the smoothing effects, and the pattern for shaping the donor cornea is based further on the smoothing effects. Obtaining the assessment of the cornea may include obtaining a topographic measurement, a tomographic measurement, anterior segment optical coherence tomography (OCT), Scheimpflug imaging, an epithelium mapping, a stromal thickness mapping, and/or one or more biomechanical measurements.

22 Claims, 2 Drawing Sheets

(51) Int. Cl.
    *B23K 26/402*       (2014.01)
    *G16H 20/40*       (2018.01)
(58) Field of Classification Search
    CPC ................ A61F 9/0081; A61F 9/00831; A61F
                2009/00872; A61F 2/145; A61F
           2009/00893; A61F 2240/004; G16H
                     20/40; A61B 3/107
    See application file for complete search history.

(56)                 References Cited

U.S. PATENT DOCUMENTS

| | | | |
|---|---|---|---|
| 2013/0268071 A1* | 10/2013 | Vilupuru | ................... A61F 9/04 |
| | | | 623/6.17 |
| 2014/0264980 A1* | 9/2014 | Muller | ................. A61F 9/0081 |
| | | | 264/1.36 |
| 2017/0027754 A1* | 2/2017 | Muller | ............... A61F 9/00812 |
| 2017/0095147 A1* | 4/2017 | Copland | ............... A61B 3/107 |

* cited by examiner

30a

30

30b epithelium 10a

Bowman's membrane 10b stroma cornea 10

100

202

Obtain assessment of cornea

2

Assessment

204

Process assessment cornea

4

Inverse
measurements

6

Instructions

206

Shape corneal tissue with laser
system based on inverse
measurements

200

30

302

Assessment system

304

Controller

20

Corneal Tissue

306

Laser system

30

Corneal implant

300

CORNEAL TREATMENT

CROSS-REFERENCE TO RELATED APPLICATIONS

This application is a National Stage Application of International Patent Application No. PCT/US2020/023331, filed Mar. 18, 2020, which claims benefit of, and priority to, U.S. Provisional Patent Application Ser. No. 62/819,769, filed Mar. 18, 2019, the contents of these applications being incorporated entirely herein by reference.

FIELD OF THE INVENTION

The present disclosure relates generally to systems and methods for correcting eye disorders, and more particularly, to systems and methods relating to implants for treating keratoconus.

BACKGROUND

Keratoconus is a degenerative disorder of the eye where the central or paracentral cornea undergoes progressive thinning and weakening of the cornea. This causes the cornea to bulge into an irregular conical shape that can distort vision.

SUMMARY

According to aspects of the present disclosure, systems and methods produce implants for treating keratoconus or similar eye disorders. According to an example embodiment, a system for producing a corneal implant includes assessment means for obtaining an assessment of a cornea of a subject. The system includes a controller including one or more processors configured to execute instructions stored on non-transitive computer readable media, the instructions causing the one or more processors to determine, based on the assessment, inverse measurements for correcting one or more irregularities associated with the keratoconus. The system includes a laser system configured to receive the inverse measurements and to shape a donor cornea according to a pattern based on the inverse measurements.

In the example system above, the instructions may further cause the one or more processors to determine smoothing effects associated with the cornea, the inverse measurements are based further on the smoothing effects, and the pattern for shaping the donor cornea may be based further on the smoothing effects.

In the example system above, the assessment means may include one or more devices configured to obtain a topographic measurement, a tomographic measurement, anterior segment optical coherence tomography (OCT), Scheimpflug imaging, an epithelium mapping, a stromal thickness mapping, and/or one or more biomechanical measurements.

In the example system above, the one or more irregularities may include an outward protrusion in the cornea of the subject. The assessment means may determine a shape and dimensions of the outward protrusion. The inverse measurements may be determined by the one or more processors to correct for the outward protrusion. The laser system may be configured to shape the donor cornea to include a thinner portion that is positionable over the protrusion and thicker portions positionable at a periphery of the protrusion.

In the example system above, the instructions may further cause the one or more processors to determine edge characteristics for the donor cornea for implantation in the cornea of the subject, and the laser system may be further configured to shape the donor cornea to include the edge characteristics.

In the example system above, the pattern for shaping the donor cornea may be a spot pattern. The laser system may include a femtosecond laser or an excimer laser.

In another example embodiment, a method for producing a corneal implant includes identifying a subject with keratoconus. The method includes obtaining, with assessment means, an assessment of a cornea of a subject. The method includes determining, by one or more processors, inverse measurements for correcting one or more irregularities associated with the keratoconus based on the assessment. The method includes shaping, with a laser system, a donor cornea according to a pattern based on the inverse measurements.

The example method above may further include determining smoothing effects associated with the cornea, wherein the inverse measurements are based further on the smoothing effects, and the pattern for shaping the donor cornea is based further on the smoothing effects.

In the example method above, obtaining the assessment of the cornea includes obtaining a topographic measurement, a tomographic measurement, anterior segment optical coherence tomography (OCT), Scheimpflug imaging, an epithelium mapping, a stromal thickness mapping, and/or one or more biomechanical measurements.

In the example method above, the one or more irregularities includes an outward protrusion in the cornea of the subject. The assessment determines a shape and dimensions of the outward protrusion. The inverse measurements correct for the outward protrusion. The donor cornea is shaped to include a thinner portion that is positionable over the protrusion and thicker portions positionable at a periphery of the protrusion.

The example method above may further include determining edge characteristics for the donor cornea for implantation in the cornea of the subject, and shaping, with the laser system, the donor cornea to include the edge characteristics.

In the example method above, the pattern for shaping the donor cornea may be a spot pattern. The laser system may include a femtosecond laser or an excimer laser.

Figure 1:
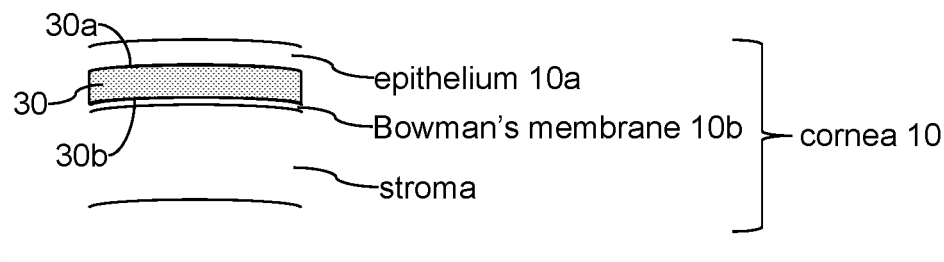
FIG. 1 illustrates a diagram of an example treatment employing a corneal implant that is shaped to correct the irregularities in a cornea caused by keratoconus, according to aspects of the present disclosure.

While the present disclosure is susceptible to various modifications and alternative forms, a specific embodiment thereof has been shown by way of example in the drawings and will herein be described in detail. It should be understood, however, that it is not intended to limit the present disclosure to the particular forms disclosed, but on the contrary, the intention is to cover all modifications, equivalents, and alternatives falling within the spirit of the present disclosure.

DESCRIPTION

FIG. 1 illustrates a diagram of an example keratoconus treatment 100 for a cornea 10. In particular, the treatment 100 employs a corneal implant 30 that is shaped to correct the irregularities in corneal shape caused by keratoconus. According to some embodiments, the implant 30 can be formed by shaping a lenticule that is cut from donor corneal tissue. The lenticule provides a more general shape (e.g., a blank) that can be subsequently reshaped into the implant 30.

As shown in FIG. 1, the implant 30 can be employed as an onlay implant that is implanted under the epithelium 20*a* and above Bowman's membrane 20*b*. In other words, the implant 30 has an anterior surface 30*a* that faces the epithelium 20*a* and a posterior surface 30*b* that faces Bowman's membrane 20*b*. In some implementations, Bowman's membrane 20*b* may be ablated by a few microns prior to receiving the implant 30.

Further aspects of producing, delivering, and implementing a corneal implant are described in U.S. Pat. No. 10,092,393, filed Jan. 10, 2014, U.S. Pat. No. 10,449,090, filed Feb. 28, 2016, U.S. Patent Application Publication No. 2017/0319329, filed May 5, 2017, International Patent Publication No. WO 2019/084557, filed Oct. 29, 2018, U.S. Patent Application Publication No. 2019/0175333, filed Dec. 13, 2018, the contents of these applications being incorporated entirely herein by reference.

Figure 2:
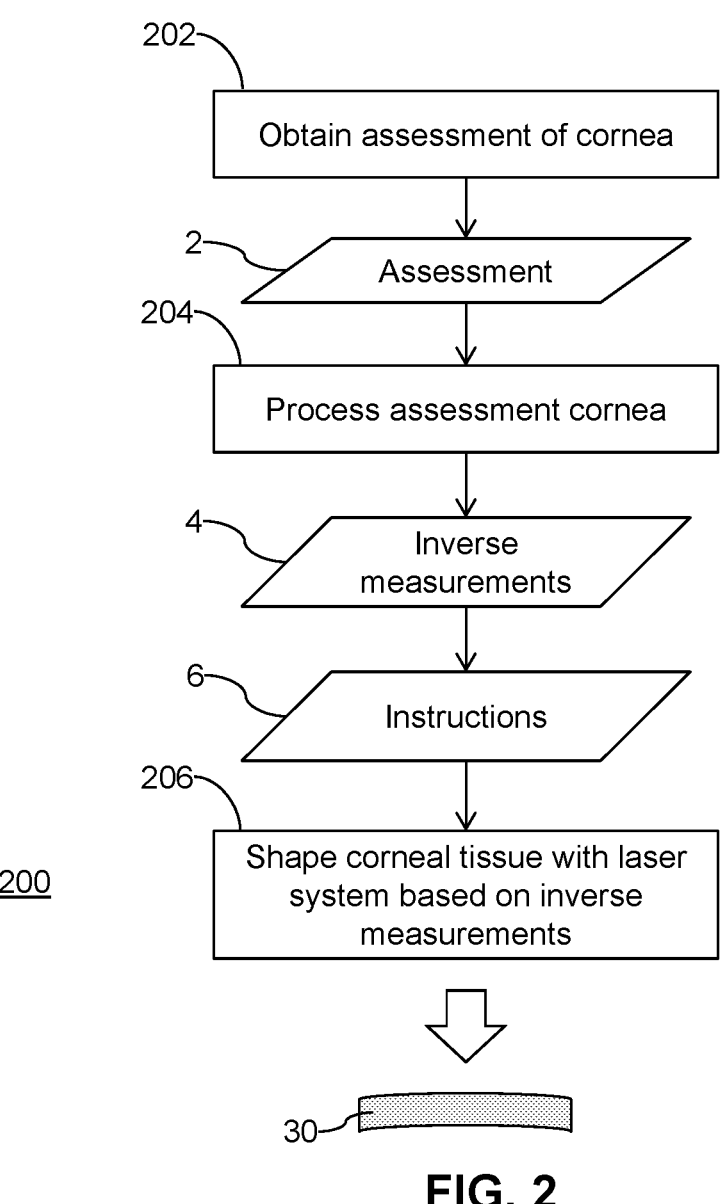
FIG. 2 illustrates an example process for determining the shape of and producing an implant to correct the irregularities in a cornea caused by keratoconus, according to aspects of the present disclosure.

FIG. 2 illustrates an example process 200 for determining the shape of and producing the implant 30. In act 202, an assessment 2 of the cornea is obtained for a subject with keratoconus. The assessment 2 may involve topographic measurements, tomographic measurements, anterior segment optical coherence tomography (OCT), Scheimpflug imaging, epithelium mapping, and stromal thickness mapping, and/or biomechanical measurements. As described above, keratoconus can cause irregularities in corneal shape, including an irregular conical shape. Such irregularities can be asymmetric, off-axis, etc. The assessment 2 captures such aspects of the irregularities. In act 204, the assessment 2 is processed to determine inverse measurements 4 for correcting the irregularities. According to one aspect, the inverse measurements 4 may reflect an inverse of topographical features that produce the irregularities, where the assessment 2 identifies such topographical features. In act 206, donor corneal tissue (e.g., a lenticule) is shaped with a laser system to produce the implant 30. The laser system is controlled by instructions 6 that receive the inverse measurements 4 as input. The instructions 6 cause a laser to be applied according to a pattern (e.g., a shot pattern) based on the inverse measurements 4. The inverse measurements 4 allow the implant 30, when implanted, to produce a new corneal shape that corrects the irregularities. Because the irregularities caused by keratoconus are unique to each individual, the inverse measurements 4 allow the implant 30 to provide a customized correction.

For instance, if a portion of the cornea has an irregularity that protrudes outwardly, the assessment 2 captures the shape and dimensions of this protrusion. The inverse measurements 4 allow the implant 30 to correct for this protrusion. In particular, when implanted, the implant 30 may include a thinner portion that aligns with (e.g., is positioned over) the protrusion and thicker portions that are positioned at a periphery of the protrusion. As such, the implant 30 has the effect of minimizing the effect of the protrusion on the corneal shape.

The shape of the implant 10 may also include desired edge characteristics and other features that allow the structure of the implant 10 to blend or transition smoothly into the surrounding eye structure, for instance, to improve optics and/or promote epithelial growth over the implant 10.

Notably, inverse measurements 4 derived from the assessment 2 accounts for the smoothing effects from the epithelium and/or other corneal structures, such as a pocket receiving the implant 10 or a flap positioned over the implant 10. If the inverse measurements 4 do not sufficiently account for these smoothing effects, the implant 10 might not provide sufficient correction for the irregularities, i.e., the resulting implant 10 may provide an under-correction. In some cases, processing the assessment 2 in act 204 to determine inverse measurements 4 for correcting the irregularities may be predicated on an interactive process that simulates correction and derives a pattern (e.g., shot pattern) for the laser in act 206.

Figure 3:
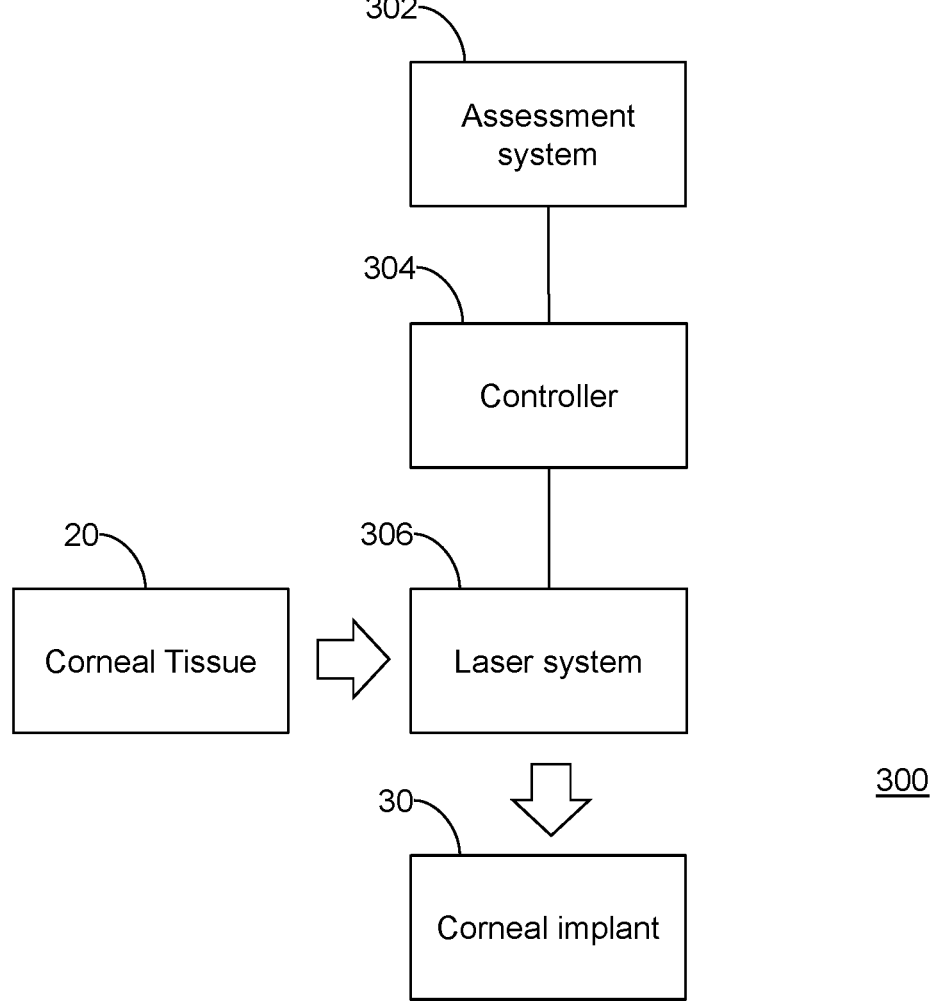
FIG. 3 illustrates an example treatment system for determining the shape of and producing an implant to correct the irregularities in a cornea caused by keratoconus, according to aspects of the present disclosure.

FIG. 3 illustrates a corresponding example treatment system 300 for determining the shape of and producing the implant 30. The treatment system 300 includes an assessment system 302 for obtaining an assessment of the cornea. The assessment system 302 may include devices for obtaining topographic measurements, tomographic measurements, anterior segment optical coherence tomography (OCT), Scheimpflug imaging, epithelium mapping, and stromal thickness mapping, and/or biomechanical measurements. The treatment system 300 also includes a controller 304 for receiving the assessment and determining the inverse measurements for the implant 30. In addition, the treatment system 300 includes a laser system 306 for cutting and shaping corneal tissue 20 (e.g., a lenticule) according to the inverse measurements to produce the implant 30. For instance, the laser system 306 may include a femtosecond laser, an excimer laser, or the like. The controller 304 may also control the laser system 306.

The controller 304 may include one or more processors configured to execute instructions stored on non-transitive computer readable media. The controller 304 may be implemented with a programmable device, such as a general purpose computer system, microprocessor, field programmable gate array (FPGA), digital signal processors (DSP), or micro-controller, that executes stored instructions. Stored on any one or on a combination of computer readable media, the instructions can be implemented as software. Such software may include, but is not limited to, device drivers, firmware, operating systems, development tools, applications software, and the like. Software may employ suitable interpretable or executable code mechanism, including but not limited to scripts, interpretable programs, dynamic link libraries (DLLs), Java classes and applets, complete executable programs, and the like. Computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

Although the examples above provide treatment for keratoconus, it is contemplated that similar approaches may be employed to produce customized implants to treat other disorders of the eye.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the invention. It is also contemplated that additional embodiments according to aspects of the present disclosure may combine any number of features from any of the embodiments described herein.

What is claimed is:

1. A system for producing a corneal implant, comprising:
an assessment device for obtaining an assessment of a cornea of a subject, wherein the assessment device includes one or more devices configured to obtain a tomographic measurement, anterior segment optical coherence tomography (OCT), Scheimpflug imaging, an epithelium mapping, and/or a stromal thickness mapping;
a controller including one or more processors configured to execute instructions stored on non-transitive computer readable media, the instructions causing the one or more processors to determine, based on the assessment of a cornea of a subject, inverse measurements for correcting one or more irregularities associated with the cornea, and smoothing effects associated with the cornea; and
a laser system configured to receive the inverse measurements and to shape a donor cornea according to a pattern based on the inverse measurements and the smoothing effects.

2. The system of claim 1, wherein, the inverse measurements are based further on the smoothing effects.

3. The system of claim 1, wherein the assessment device includes one or more devices configured to obtain a topographic measurement.

4. The system of claim 1, wherein the one or more irregularities includes an outward protrusion in the cornea of the subject, the assessment device determines a shape and dimensions of the outward protrusion, the inverse measurements determined by the one or more processors correct for the outward protrusion, and the laser system is configured to shape the donor cornea to include a thinner portion that is positionable over the outward protrusion and thicker portions positionable at a periphery of the outward protrusion.

5. The system of claim 1, wherein the instructions further cause the one or more processors to determine edge characteristics for the donor cornea for implantation in the cornea of the subject, and the laser system is configured to shape the donor cornea to include the edge characteristics.

6. The system of claim 1, wherein the pattern for shaping the donor cornea is a spot pattern.

7. The system of claim 1, wherein the laser system includes a femtosecond laser or an excimer laser.

8. The system of claim 1, wherein the assessment device includes one or more devices configured to obtain one or more biomechanical measurements.

9. The system of claim 1, wherein the one or more irregularities are associated with keratoconus.

10. The system of claim 1, wherein the assessment device is configured to obtain the anterior segment OCT.

11. The system of claim 1, wherein the assessment device is configured to obtain Scheimplug imaging.

12. The system of claim 1, wherein the smoothing effects are one or both of an optical effect caused by a transition from the corneal implant into a surrounding eye structure after the corneal implant has been implanted, and epithelial growth over the corneal implant after the corneal implant has been implanted.

13. A method for producing a corneal implant, comprising:
identifying a subject with one or more irregularities associated with a cornea;
receiving, from assessment device, an assessment of the cornea of the subject, wherein the assessment device includes a tomographic measurement, anterior segment optical coherence tomography (OCT), Scheimpflug imaging, an epithelium mapping, and/or a stromal thickness mapping;
determining smoothing effects associated with the cornea;
determining, by one or more processors, inverse measurements for correcting the one or more irregularities associated with the cornea based on the assessment; and
shaping, with a laser system, a donor cornea according to a pattern based on the inverse measurements and the smoothing effects.

14. The method of claim 13, wherein the inverse measurements are based further on the smoothing effects.

15. The method of claim 13, wherein the assessment of the cornea includes at least one of a topographic measurement, a tomographic measurement, or anterior segment optical coherence tomography (OCT).

16. The method of claim 13, wherein the one or more irregularities includes an outward protrusion in the cornea of the subject, the assessment determines a shape and dimensions of the outward protrusion, the inverse measurements correct for the outward protrusion, and the donor cornea is shaped to include a thinner portion that is positionable over the outward protrusion and thicker portions positionable at a periphery of the outward protrusion.

17. The method of claim 13, further comprising determining edge characteristics for the donor cornea for implantation in the cornea of the subject, and shaping, with the laser system, the donor cornea to include the edge characteristics.

18. The method of claim 13, wherein the pattern for shaping the donor cornea is a spot pattern.

19. The method of claim 13, wherein the laser system includes a femtosecond laser or an excimer laser.

20. The method of claim 13 wherein the assessment of the cornea includes one or more biomechanical measurements.

21. The method of claim 13, wherein the one or more irregularities are associated with keratoconus.

22. The method of claim 13, wherein the smoothing effects are one or both of an optical effect caused by a transition from the corneal implant into a surrounding eye structure after the corneal implant has been implanted, and epithelial growth over the corneal implant after the corneal implant has been implanted.

* * * * *